(12) United States Patent
Pouliot et al.

(10) Patent No.: US 7,804,936 B2
(45) Date of Patent: Sep. 28, 2010

(54) DOSE-GUIDED RADIATION THERAPY USING CONE BEAM CT

(75) Inventors: Jean Pouliot, Mill Valley, CA (US); Josephine Chen, Oakland, CA (US); Hong Chen, San Francisco, CA (US); Juan Carlos Celi, Bensheim (DE); Ali Bani-Hashemi, Walnut Creek, CA (US); Bijumon Gangadharan, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 355 days.

(21) Appl. No.: 11/824,404

(22) Filed: Jun. 28, 2007

(65) Prior Publication Data

US 2009/0003512 A1 Jan. 1, 2009

(51) Int. Cl.
*A61N 5/10* (2006.01)
(52) U.S. Cl. .................................................. 378/65
(58) Field of Classification Search ............... 378/4, 378/65

See application file for complete search history.

(56) References Cited

U.S. PATENT DOCUMENTS

| | | | | |
|---|---|---|---|---|
| 2001/0033682 A1* | 10/2001 | Robar et al. | ............... | 382/132 |
| 2002/0027971 A1* | 3/2002 | Deasy et al. | ................. | 378/65 |
| 2003/0007601 A1* | 1/2003 | Jaffray et al. | ................. | 378/65 |
| 2003/0072410 A1* | 4/2003 | Siochi | ......................... | 378/65 |
| 2003/0091146 A1* | 5/2003 | Siochi | ......................... | 378/65 |
| 2004/0001569 A1* | 1/2004 | Luo | ............................. | 378/65 |
| 2004/0120452 A1* | 6/2004 | Shapiro et al. | ............... | 378/19 |
| 2004/0190680 A1* | 9/2004 | Chang | ......................... | 378/65 |
| 2005/0058237 A1* | 3/2005 | Morf | .............................. | 378/4 |
| 2005/0207531 A1* | 9/2005 | Dempsey et al. | ............. | 378/65 |
| 2006/0008046 A1* | 1/2006 | Ruhrnschopf | .................. | 378/7 |

OTHER PUBLICATIONS

Chen et al., Dose-guided radiation therapy with megavoltage cone-beam CT, The British Journal of Radiology, 79, 2006, pp. S87-S98.*
Pouliot et al., Low-dose megavoltage cone-beam CT for Radiation Therapy, Int. J. Radiation Oncology Biol. Phys., vol. 61, No. 2, 2005, pp. 552-560.*
Morin et al., Dose Calculation Using Megavoltage Cone-beam CT, Int. J. Radiation Oncology Biol. Phys., vol. 67, No. 4, 2007, pp. 1201-1210.*
Spies, On scatter in megavoltage X-ray transmission imaging, ISBN 3-18-319317-5, 2000, pp. 1-79.*
Partridge et al., The practical implementation of a scatter model for portal imaging at 10 MV, Phys Med Biol, 43, 1998, pp. 2685-2693.*
Spies et al., An iterative algorithm for reconstructing incident beam distributions from transmission measurements using electronic portal imaging, Phys Med Biol, 46, 2001, pp. N203-N211.*

(Continued)

*Primary Examiner*—Edward J Glick
*Assistant Examiner*—Alexander H Taningco (57) ABSTRACT

A system includes acquisition of a three-dimensional cone beam image, and determination of a dose to be delivered based on the three-dimensional image and on parameters of a treatment beam to deliver the dose. Some systems may include modification of a three-dimensional cone beam image to correct for scatter radiation, and determination of a dose based on the modified three-dimensional cone beam image.

19 Claims, 11 Drawing Sheets

OTHER PUBLICATIONS

Rehbinder et al., Adaptive radiation therapy for compensation of errors in patient setup and treatment delivery, Phys Med, 34, 12, 2004, pp. 3363-3371.*

Yan et al., Adaptive radiation therapy, Phys Med Biol., 42, 1997, pp. 123-132.*

Morin et al., Evaluation of the Mechanical Stability of a Mega-Voltage Imaging System using a New Flat Panel Positioner, Medical Imaging: Physics of Medical Imaging, Proceedings of SPIE, vol. 5745, 2005, pp. 704-710.*

Pouliot, Jean Ph.D. et al., "Low-Dose Megavoltage Cone-Beam CT for Radiation Therapy", Int. J. Radiation Oncology Biol. Phys. vol. 61, No. 2, pp. 552-560, 2005, Copyright © Elsevier Inc. ISSN: 3060-3016.

Chen, Josephine et al., "Calibration of an amorphous-silicon flat panel portal imager for exit-beam dosimetry", Medical Physics. vol. 33, No. 3, Mar. 2006, © 2006 Am. Assoc. Phys. Med. ISSN: 0094-2405, pp. 584-594.

* cited by examiner

$R_{u,v} = P_\theta R_{x,y,z}$

DOSE-GUIDED RADIATION THERAPY USING CONE BEAM CT

BACKGROUND

1. Field

The embodiments described below relate generally to the delivery of radiation to a patient. More specifically, some embodiments are directed to determining a spatial dose distribution based on a three-dimensional image generated using a megavoltage radiation beam.

2. Description

According to conventional radiation therapy, a beam of radiation is directed toward a tumor located within a patient. The radiation beam delivers a predetermined dose of therapeutic radiation to the tumor according to an established treatment plan. The delivered radiation kills cells of the tumor by causing ionizations within the cells.

Recent advances in fractionated external beam radiation therapy, such as three-dimensional conformal and intensity-modulated radiation therapy (IMRT), have increased the ability to deliver radiation doses that conform tightly to a target volume. This tight conformance results in steep dose gradients inside the volume. For example, IMRT can create a dose gradient of 10% $mm^{-1}$ inside a target volume.

A treatment plan is designed assuming that a target volume will be in a particular position relative to a beam source during treatment. If the relevant portions are not positioned exactly as required by the treatment plan, the steep gradient may occur within sensitive healthy tissue surrounding the volume. Thus, it is increasingly important to precisely position the target volume with respect to the beam source.

Currently, internal bony markers, external markers and patient-immobilizing masks and casts are used to reproduce a desired skeletal position of the patient with respect to the beam source. However, the effectiveness of these alignment and immobilization techniques is limited by changes in the tumor location (as well as the locations of adjacent internal organs) relative to the markers. For example, the prostate can shift up to 1 cm relative to the pelvic bones due to variations in rectal/bladder filling. A tumor may shrink and the patient may lose significant weight, also causing the tumor to shift with respect to internal and external markers.

Portal images, which are projection images of the treatment field within the patient, are currently used to confirm the patient position and verify proper irradiation of the tumor. An electronic portal imaging device (EPID) may acquire a digital portal image that is used to adjust the patient position before each daily treatment. For example, using implanted gold markers to locate the prostate, daily portal imaging has been used to position the prostate with 1-2 mm accuracy.

The effectiveness of portal image-based positioning is limited, however, because implanted markers are needed to visualize soft tissue and because the full three-dimensional volume to which radiation will be delivered is inadequately represented by a two-dimensional portal image. Therefore, considerable research now focuses on providing three-dimensional imaging of the patient immediately prior to treatment delivery (i.e., when the patient is on the treatment table). Systems attempting to provide such imaging include: (1) a "CT on rails" system, requiring an additional diagnostic computed tomography machine in the treatment room; (2) a kilovoltage cone beam CT (kVCBCT) system, consisting of an additional kilovoltage X-ray source and detector attached to a treatment gantry; (3) a megavoltage cone beam CT (MVCBCT) system using the pre-existing treatment machine and an EPID for imaging; (4) a MVCT system, using the pre-existing treatment machine with an attached arc of detectors; and (5) a tomotherapy system, replacing the traditional treatment machine with a CT ring and a MV beam source.

An IGRT system may use any of the foregoing imaging modalities to translate and rotate a patient to a position required by a treatment plan. These imaging modalities may also be used to modify radiation delivery to account for changing relative positions of internal organs and changing shapes of the organs between treatment fractions. In this case, a pre-treatment image may be acquired and the treatment beam may be adjusted based thereon immediately before irradiation.

Images acquired in the treatment room may also be used to adjust the treatment beam in situations where organs are expected to move significantly during treatment. For these situations, beam delivery may be halted when the target volume is out of a certain acceptable region, or the beam may track the target volume during irradiation using specially-designed mobile linear accelerators.

If the dose that was delivered in previous fractions can be estimated, the treatment plan for future fractions may be modified to compensate for prior dosimetric errors. This "dose-guided radiation therapy" (DGRT) could correct for errors due to patient anatomical changes as well as machine delivery errors. However, current methods to determine delivered or to-be-delivered doses are inefficient and/or inaccurate.

According to some current methods, diodes or thermoluminescent dosimeters are placed on the patient surface and/or implantable MOSFET dosimeters are embedded within critical internal structures. The time and effort required to place or implant such devices limits their use during treatment. More importantly, these techniques provide only point dose measurements, which are not suitable for determining dose distributions based on which future fractions may be modified.

What is needed is an efficient system to determine a three-dimensional dose distribution. Such a method may detect dosimetric errors produced by machine delivery errors, patient positioning errors, and/or variations over time in organ positions and shapes.

SUMMARY

To address at least the foregoing, some embodiments provide a system, method, apparatus, and means to acquire a three-dimensional megavoltage cone beam image, and determine a dose to be delivered based on the three-dimensional image and on parameters of a treatment beam to deliver the dose. The parameters of the treatment beam may be changed to second parameters based on the determined dose. In some aspects, acquisition of the three-dimensional megavoltage cone beam image includes acquisition of a plurality of two-dimensional images using megavoltage radiation, and generation of a three-dimensional image based on the plurality of two-dimensional images.

According to some aspects, a three-dimensional megavoltage cone beam image is modified to correct for scatter radiation, and a dose is determined based on the modified three-dimensional megavoltage cone beam image. A next treatment fraction may be changed based on the determined dose in some aspects.

Modification of the three-dimensional megavoltage cone beam image to correct for scatter radiation may include acquisition of a plurality of two-dimensional images using megavoltage radiation, modification of each of the plurality of two-dimensional images to correct for scatter radiation, and generation of the three-dimensional megavoltage cone beam image based on the modified two-dimensional images.

In some aspects, modification of the three-dimensional megavoltage cone beam image includes determination of a geometric model of correction factors to characterize a cupping artifact of scatter radiation, and modification of the three-dimensional megavoltage cone beam image based on the geometric model.

In other aspects, modification of the three-dimensional megavoltage cone beam image includes registration of the three-dimensional megavoltage cone beam image with a previously-acquired three-dimensional image, determination of a plurality of voxel ratios based on image values of each of a plurality of voxels of the previously-acquired three-dimensional image and image values of each of a plurality of associated voxels of the registered three-dimensional image, determination of a volume ratio associated with each of a plurality of volumes of the registered three-dimensional image, wherein each of the volume ratios is based on a plurality of the determined voxel ratios, and modification of each of the plurality of volumes of the registered three-dimensional image by an associated volume ratio.

Determination of the dose according to some aspects may include determination of an electron density value associated with each of a plurality of voxels of the modified three-dimensional megavoltage cone beam image, delivery of a treatment radiation beam, acquisition of portal images during delivery of the treatment radiation beam, determination of a map of treatment beam energy fluence based on the portal images, determination of an entry dose based on the map of treatment beam energy fluence and the electron density value associated with each of the plurality of voxels, and determination of the dose delivered to each of the plurality of voxels based on the entry dose and the electron density value associated with each of the plurality of voxels.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated by the inventors for carrying out the described embodiments. Various modifications, however, will remain readily apparent to those in the art.

Figure 1:
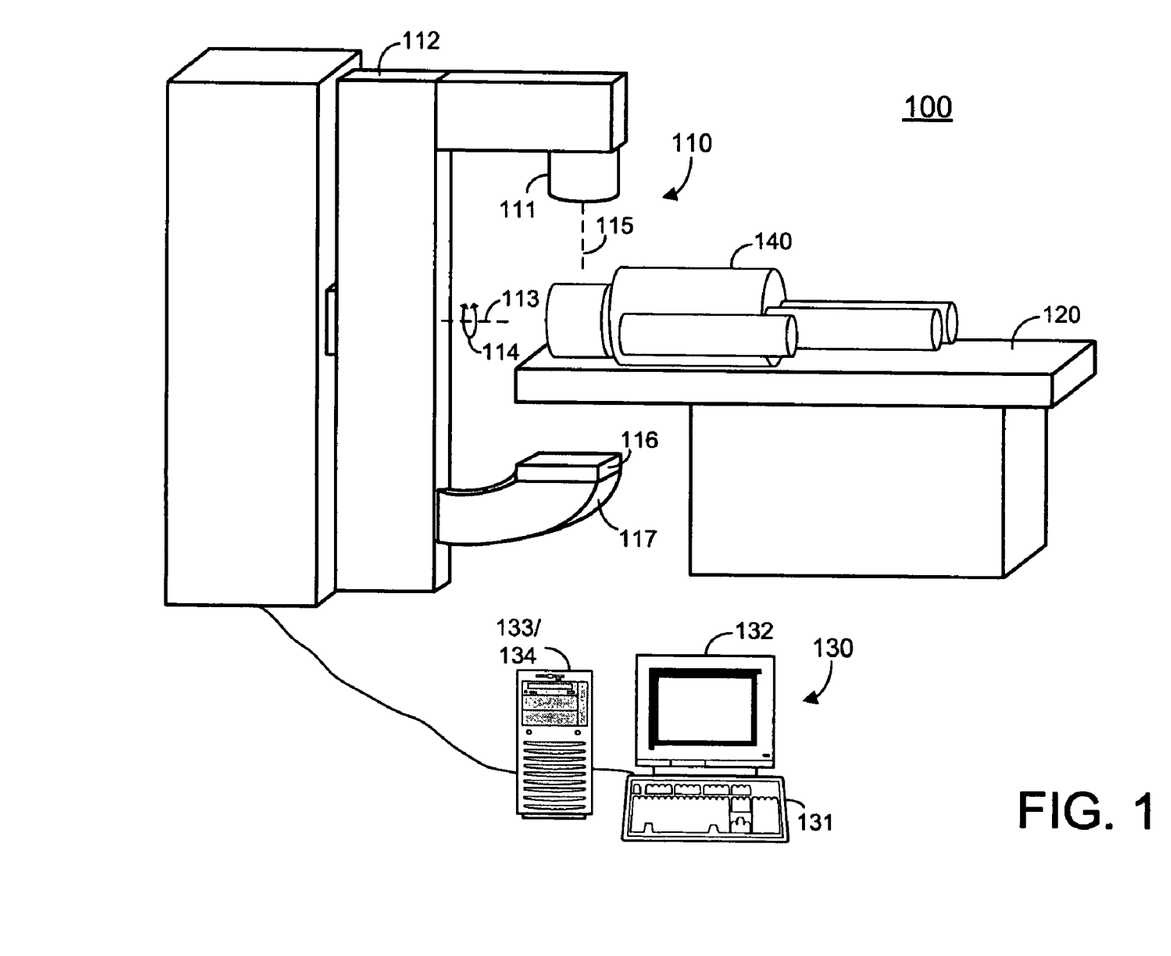
FIG. 1 is a perspective view of a radiation treatment room according to some embodiments.

FIG. 1 illustrates radiation treatment room 100 pursuant to some embodiments. Radiation treatment room 100 includes linear accelerator (linac) 110, table 120 and operator console 130. The elements of radiation treatment room 100 may be used to deliver radiation to a target volume of beam object 140. In this regard, beam object 140 may comprise a patient positioned to receive radiation according to a radiation treatment plan. The elements of treatment room 100 may be employed in other applications according to some embodiments.

Linac 110 generates and emits the radiation, and is primarily composed of treatment head 111 and gantry 112. Treatment head 11 includes a beam-emitting device (not shown) for emitting a radiation beam used during calibration, verification, and/or treatment. The radiation beam may comprise electron, photon or any other type of radiation. According to some embodiments, the radiation beam exhibits energies in the megavoltage range (i.e. >1 MeV) and may therefore be referred to as megavoltage radiation. Also included within treatment head 111 is a beam-shielding device, or collimator (not shown) for shaping the beam and for shielding sensitive surfaces from the beam.

Treatment head 111 is coupled to a projection of gantry 112. Gantry 112 is rotatable around gantry axis 113 before, during and after radiation treatment. As indicated by arrow 114, gantry 112 may rotate clockwise or counter-clockwise according to some embodiments. Rotation of gantry 112 serves to rotate treatment head 111 around axis 113.

During radiation treatment, a radiation beam is emitted from treatment head 111 as a divergent beam. The beam is emitted towards an isocenter of linac 110. The isocenter is located at the intersection of beam axis 115 and gantry axis 113. Due to divergence of the radiation beam and the shaping of the beam by the aforementioned beam-shaping devices, the beam may deliver radiation to a volume of beam object 140 rather than only to the isocenter.

Table 120 supports beam object 140 during radiation treatment. Table 120 may be adjustable to assist in positioning a treatment area of beam object 140 at the isocenter of linac 110. Table 120 may also be used to support devices used for such positioning, for calibration and/or for verification.

Imaging device 116 may acquire images before, during and/or after radiation treatment. For example, imaging device 116 may be used to acquire images for verification and recordation of a target volume position and of an internal patient portal to which radiation is delivered.

Imaging device 116 may be attached to gantry 112 in any manner, including via extendible and retractable housing 117. Rotation of gantry 112 may cause treatment head 111 and imaging device 116 to rotate around the isocenter such that isocenter remains located between treatment head 111 and imaging device 116 during the rotation.

Imaging device 116 may comprise any system to acquire an image based on received megavoltage photon radiation. In a case that linac 110 is capable of producing kilovoltage photon radiation via beamline modification or other techniques, imaging device 116 may also acquire images based on such kilovoltage radiation. In some embodiments, imaging device 116 is a flat-panel imaging device using a scintillator layer and solid-state amorphous silicon photodiodes deployed in a two-dimensional array. In operation, the scintillator layer receives photons and generates light in proportion to the intensity of the received photons. The array of photodiodes receives the light and records the intensity of received light as stored electrical charge.

In other embodiments, imaging device 116 converts received photons to electrical charge without requiring a scintillator layer. The photons are absorbed directly by an array of amorphous selenium photoconductors. The photoconductors convert the photons directly to stored electrical charge. Imaging device 116 may also comprise a CCD or tube-based camera. Such an imaging device may include a light-proof housing within which are disposed a scintillator, a mirror, and a camera.

The charge developed and stored by imaging device 116 represents radiation intensities at each location of a radiation field produced by a beam emitted from treatment head 111. Since object 140 is located between treatment head and imaging device 116, the radiation intensity at a particular location represents the attenuative properties of tissues along a divergent line between a radiation source in treatment head 111 and the particular location. The set of radiation intensities acquired by imaging device 116 may therefore comprise a two-dimensional projection image of these tissues.

Operator console 130 includes input device 131 for receiving instructions from an operator and output device 132, which may be a monitor for presenting operational parameters of linac 110 and imaging device 116 and/or interfaces for receiving instructions. Output device 132 may also present a two-dimensional projection image, a three-dimensional megavoltage (or kilovoltage) cone beam image and/or two-dimensional "slice" images based on the three-dimensional image.

Input device 131 and output device 132 are coupled to processor 133 and storage 134. Processor 133 may execute program code to perform any of the determinations and generations described herein, and/or to cause linac 110 to perform any of the process steps described herein.

Storage 134 may also store program code to generate and/or modify a treatment plan according to some embodiments. Such code may comprise the COHERENCE™ workspace or the KONRAD™ treatment planning system sold by Siemens Medical Solutions. Accordingly, storage 134 may also store radiation treatment plans in accordance with any currently—or hereafter—known format. The treatment plans may comprise scripts that are automatically executable by elements of room 100 to provide radiation therapy fractions. Each fraction of each treatment plan may require a patient to be positioned in a particular manner with respect to treatment head 111.

Operator console 130 may be in a room other than treatment room 100, in order to protect its operator from radiation. For example, treatment room 100 may be heavily shielded, such as a concrete vault, to shield the operator from radiation generated by linac 110.

Figure 2:
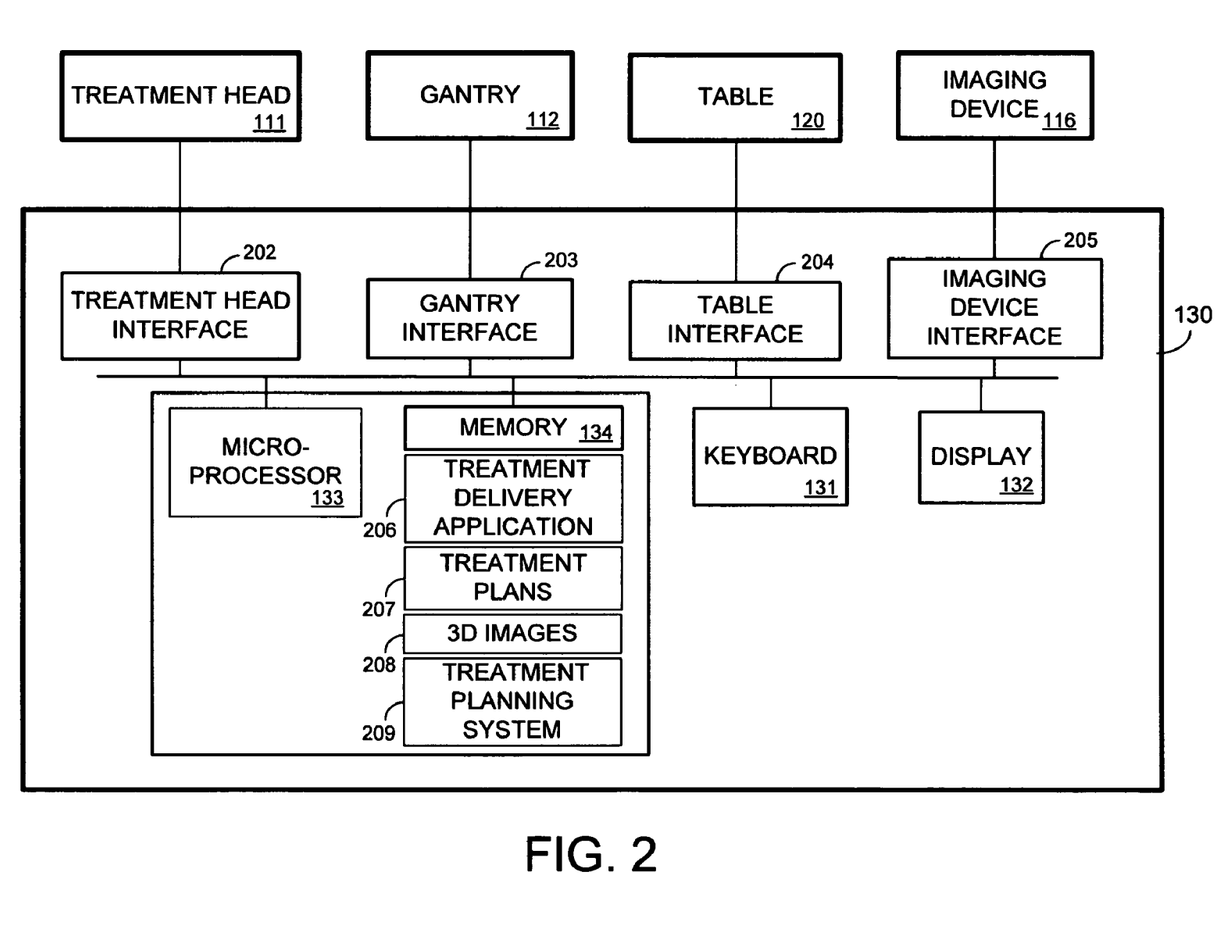
FIG. 2 is a block diagram of the internal architecture of radiation treatment room devices according to some embodiments.

FIG. 2 is a block diagram of elements of treatment room 100 according to some embodiments. The illustrated elements may be implemented by any suitable combination of hardware, software and/or firmware.

Operator console 130 includes interfaces 202, 203, 204 and 205 for interfacing with respective elements 111, 112, 120 and 116 of treatment room 100. Each of the interfaces may comprise any suitable type of hardware and/or software interface, and may or may not be proprietary. Operator console 130 may control the various elements through the interfaces and based on instructions from processor 133.

Microprocessor 133 executes processor-executable process steps stored in storage 134 to provide operation according to some embodiments. These process steps may comprise treatment delivery application 206 to execute one of treatment plans 207. Treatment delivery application 206 may, in some embodiments, be used to calibrate imaging device 116, to acquire projection images, to generate a three-dimensional image based on the projection images, and to determine a dose based on the three-dimensional image. Storage 134 may also comprise three-dimensional images 208 generated in conjunction with the foregoing process steps and treatment planning system 209 for modifying treatment plans 207 based on the foregoing.

A hardware environment according to some embodiments may include less or more elements than those shown in FIGS. 1 and 2. In addition, embodiments are not limited to the devices and/or to the illustrated environment. For example, some embodiments include another type of image acquisition device to acquire projection images.

Figure 3:
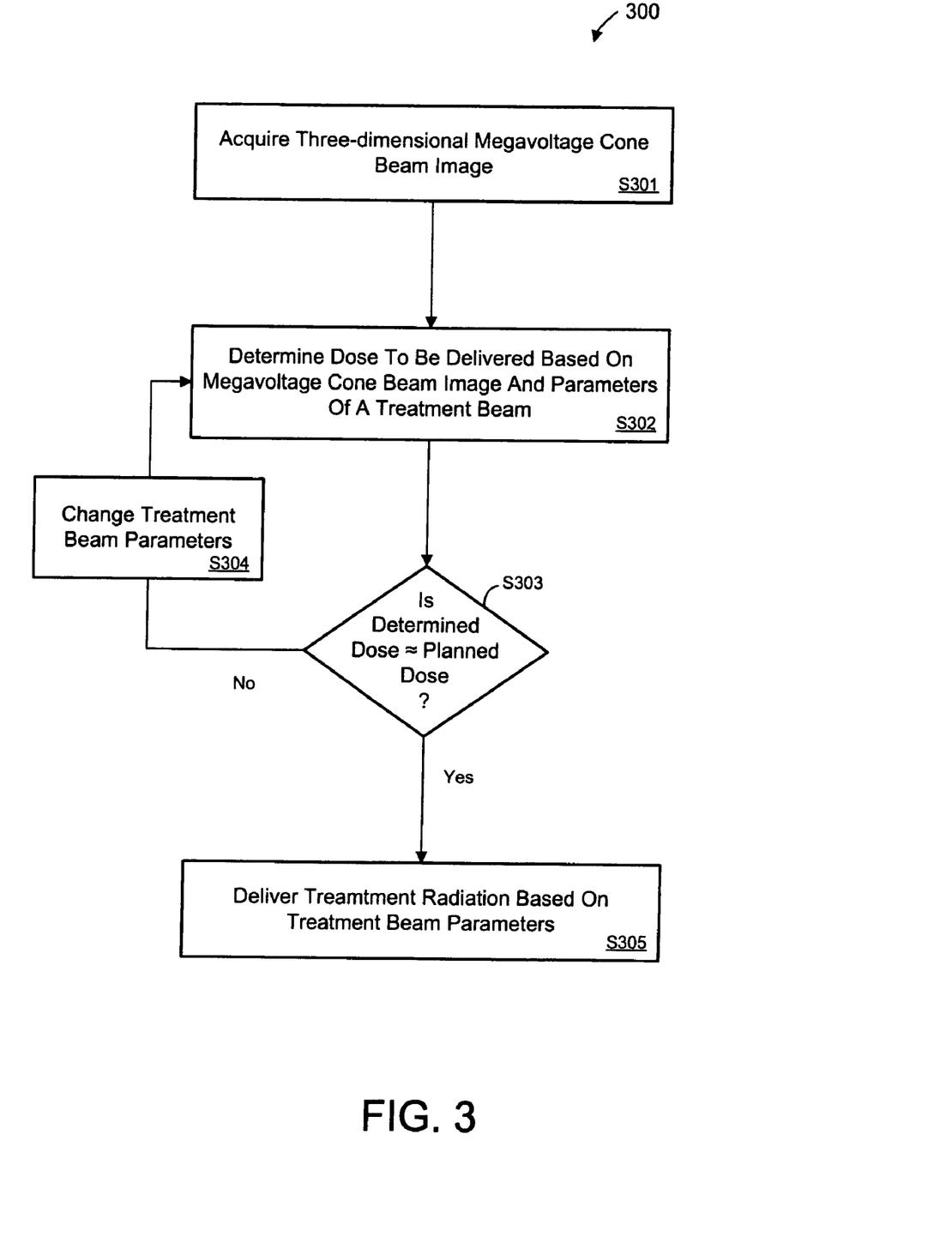
FIG. 3 comprises a flow diagram illustrating process steps according to some embodiments.

FIG. 3 is a flow diagram of a process according to some embodiments. Process 300 and the other processes described herein may be performed using any suitable combination of hardware, software or manual means. Software embodying these processes may be stored by any medium, including a fixed disk, a floppy disk, a CD-ROM, a DVD-ROM, a Zip™ disk, a magnetic tape, or a signal. Examples of these processes will be described below with respect to the elements of treatment room 100, but embodiments are not limited thereto.

Process 300 may be performed after a patient has been placed on a treatment table and is awaiting treatment. In some embodiments, process 300 may comprise a verification process to determine whether a dose to be delivered to the patient is suitably similar to a planned dose. Process 300 may also be used to alter a treatment plan if the determined dose is not suitably similar to the planned dose.

Initially, a three-dimensional megavoltage cone beam image is acquired at S301. The three-dimensional megavoltage cone beam image may be acquired using any system or systems that are or become known. According to some embodiments, acquisition of the three-dimensional image includes acquisition of a plurality of two-dimensional projection images and generation of the thee-dimensional image based on the plurality of two-dimensional images.

Some embodiments of the processes described herein may operate in conjunction with a three-dimensional kilovoltage cone beam image instead of a three-dimensional megavoltage cone beam image as described.

Figure 4:
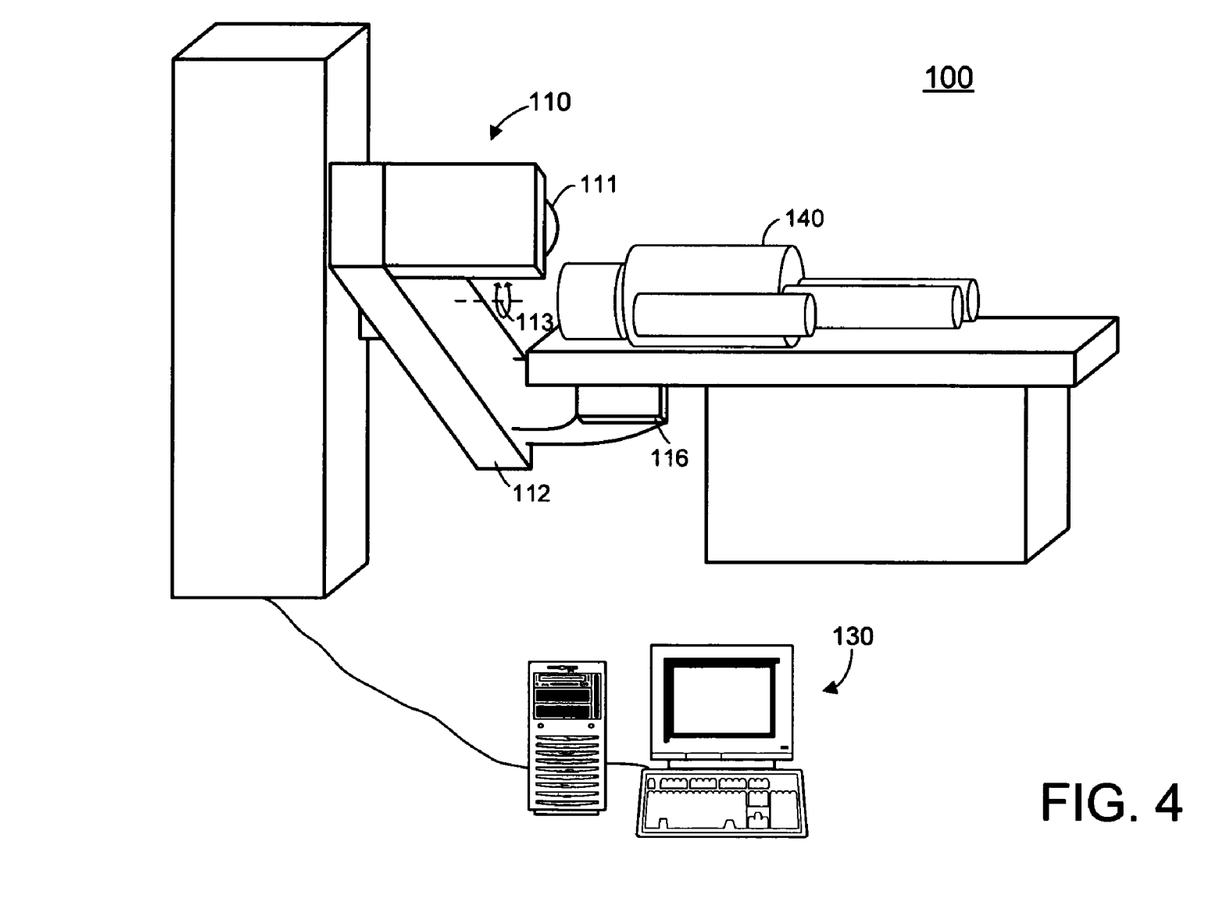
FIG. 4 is a perspective view of a radiation treatment room according to some embodiments.

With respect to FIG. 1, operator console 130 may instruct gantry 112 at S301 to rotate around axis 113. At each of several rotational angles, treatment head 111 may emit megavoltage radiation and imaging device 116 may acquire an associated projection image. FIG. 4 illustrates treatment room 100 after rotation of gantry 112 from the position illustrated in FIG. 1. As shown, treatment head 111 and imaging device 116 rotate around the isocenter and substantially maintain a physical relationship therebetween during the rotation. As a result, the projection images represent a same volume of object 140, albeit from different perspectives.

The plurality of projection images may be subjected to known corrections prior to generation of the three-dimensional image. These corrections may comprise offset correction to account for dark current effects, gain correction to account for variations in pixel sensitivity, and dead pixel correction to account for malfunctioning pixels.

Figure 5:
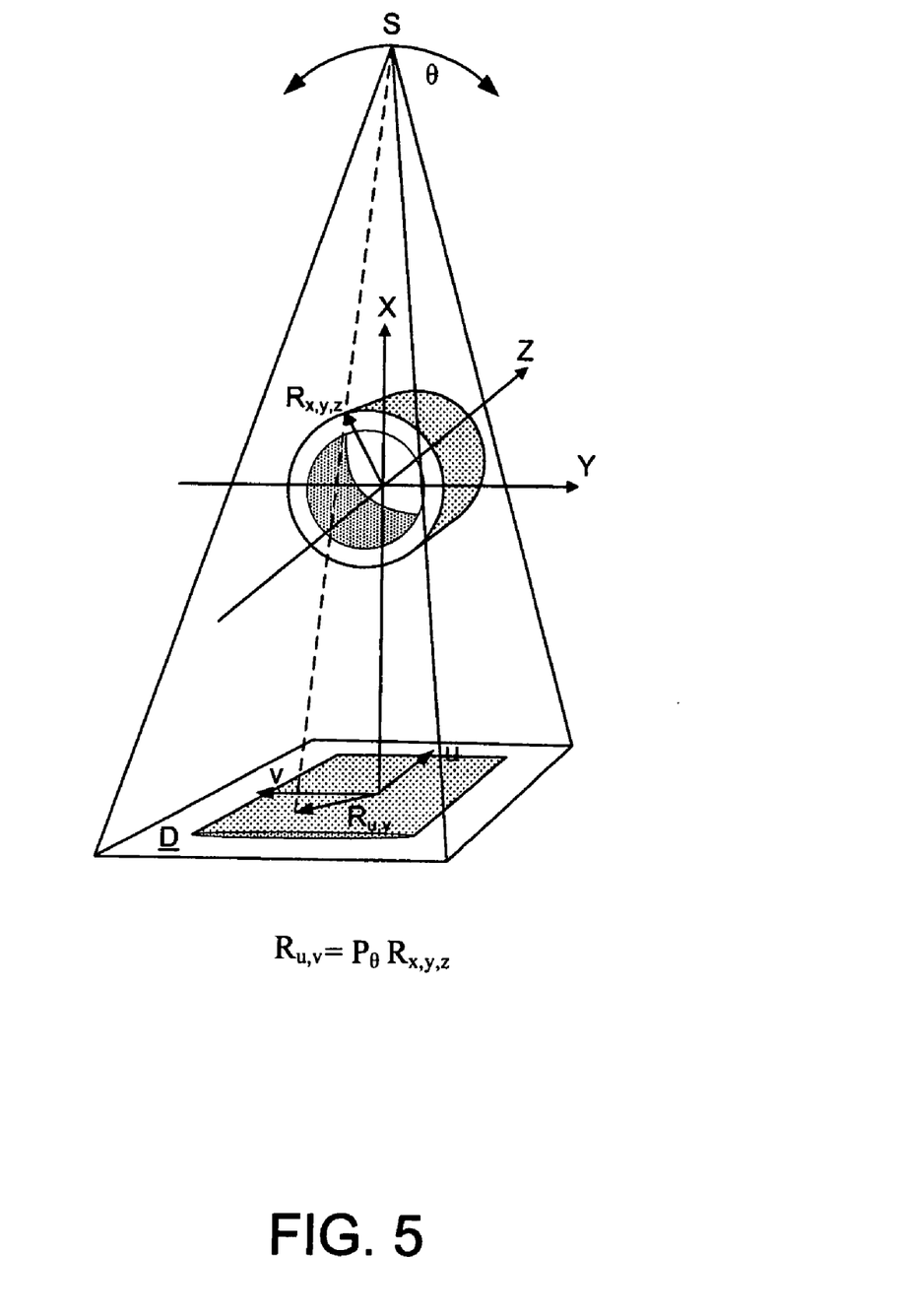
FIG. 5 is a diagram illustrating geometric calibration according to some embodiments.

Generation of the three-dimensional image based on the two-dimensional projection images may proceed according to any system that is or becomes known. According to some embodiments, this generation takes into account shifting of the imaging device and the beam source from their ideal positions due to mechanical sagging during the above-described rotation. FIG. 5 depicts geometric calibration of beam source S and detector plane D of the imaging device in some embodiments of S301. The calibration may result in a set of projection matrices P that map a point in space $R_{XYZ}$ to a projected point $R_{UV}$ on the detector plane D.

As described above, the acquired two-dimensional portal images may represent radiation intensities at each location of a radiation field. During some embodiments of S201, these radiation intensities are converted to physical electron densities prior to generation of the three-dimensional megavoltage cone beam image. Some embodiments, on the other hand, generate the three-dimensional image based on the acquired two-dimensional portal images and convert radiation intensities of the generated three-dimensional image to physical electron densities. In order to perform either type of conversion, linac 110 may be calibrated prior to process 300 to determine a physical electron density corresponding to each of several sensed radiation intensities.

Figure 6:
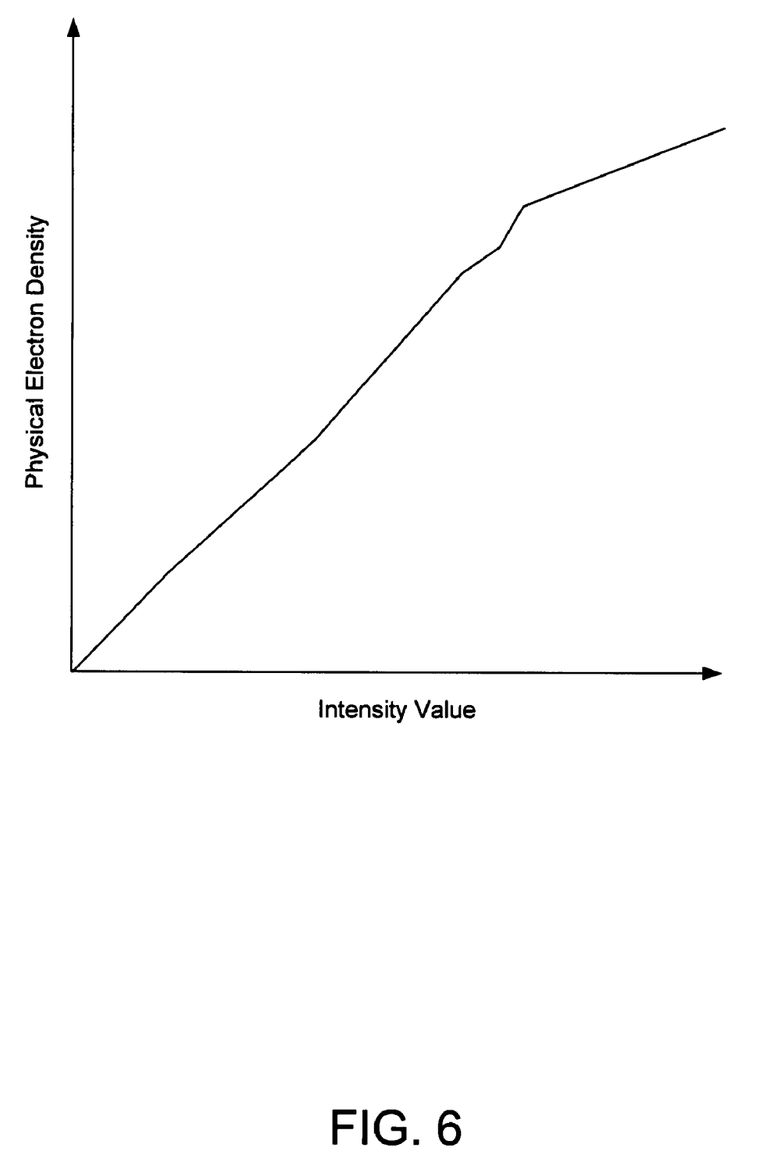
FIG. 6 is a graph illustrating relationships between physical electron densities and voxel intensity values according to some embodiments.

In some embodiments, a phantom is placed on table 120 and projection images thereof are acquired. The phantom includes materials having known physical electron densities (e.g., lung tissue, water, muscle, trabecular bone, dense bone). The projection images are analyzed to determine radiation intensities associated with each material. Accordingly, a mapping may be generated to associate the radiation intensities with the known physical electron densities. FIG. 6 illustrates such a mapping according to some embodiments.

Acquisition of the three-dimensional megavoltage cone beam image at S201 may also comprise modifying a three-dimensional image to correct for scatter radiation. Several methods for scatter correction will be described in detail below. As will be described, modification of the three-dimensional image to correct for scatter radiation may comprise correcting the two-dimensional projection images for scatter radiation prior to generation of the three-dimensional megavoltage cone beam image, or may comprise directly modifying a generated three-dimensional cone beam image to correct for scatter.

Returning to process 300, a dose to be delivered is determined at S302 based on the acquired three-dimensional megavoltage cone beam image and parameters of a treatment beam. The parameters may be stored among treatment plans 207 and may specify a beam type, a beam energy, a beam shape, and/or a beam duration. Embodiments are not limited to these beam parameters.

The dose may be determined at S302 using any conventional or hereafter-known dose calculation engine. Treatment planning system 209 may comprise a suitable dose calculation engine. Such an engine may receive beam parameters and a three-dimensional representation of physical electron densities (i.e., the megavoltage cone beam image acquired at S301) and calculate a spatial dose distribution based thereon.

Next, at S303, it is determined whether the dose is acceptably similar to a planned dose. The planned dose may be specified by the applicable treatment plan of treatment plans 208. Whether or not the determined dose is acceptably similar to the planned dose may depend upon the nature and degree of any differences between the determined dose and the planned dose. For example, the dose may be acceptably similar to a planned dose if the difference does not include a large dose received by a critical structure. The determination at S303 may be performed automatically based on pre-configured rules and/or may require operator judgment.

Figure 7:
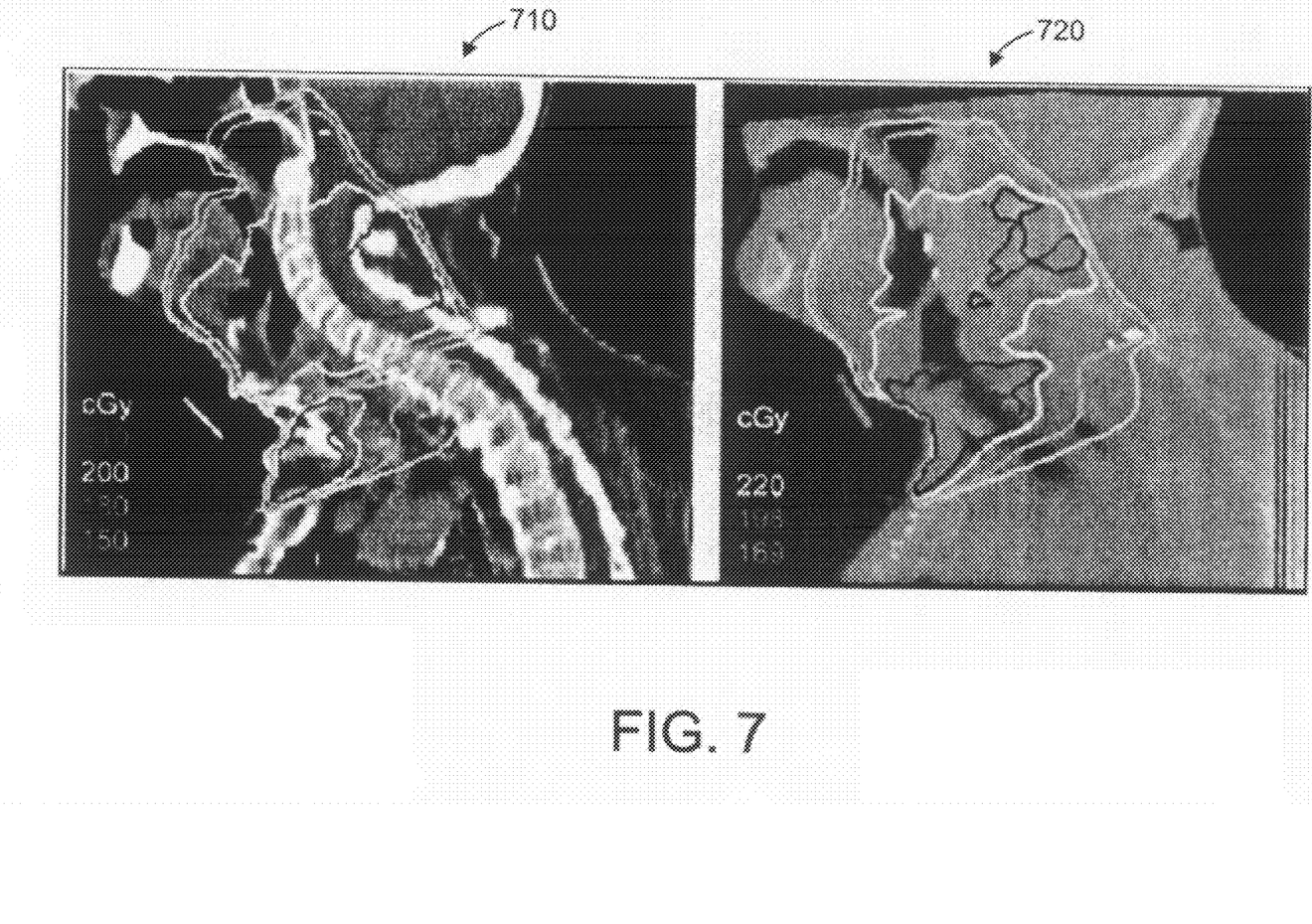
FIG. 7 depicts a planned dose profile and a calculated dose profile according to some embodiments.

FIG. 7 illustrates images 710 and 720 that may be used during the determination at S303 according to some embodiments. Output device 132 of operator console 130 may display images 710 and 720 in some embodiments. Image 710 shows isodose curves superimposed on a two-dimensional "slice" of a three-dimensional image. The three-dimensional image may comprise a CT image acquired by a conventional CT scanner for treatment planning purposes. In this regard, the isodose curves may be generated by a treatment planning system.

Image 720 represents a dose determined at S302. Image 720 includes isodose curves to depict the determined dose. The isodose curves are superimposed on a two-dimensional slice image of the three-dimensional image acquired at S301. According to some embodiments, the determined dose may be spatially registered with a planned dose, and a difference between the spatially-registered determined dose and the planned dose is determined. The spatial registration may comprise a rigid-body transformation including three-dimensional translation and rotation. It may also include a deformable registration that aligns corresponding organs by means of warping/morphing the images. The isodose curves of image 710 and 720 may be determined and displayed in any suitable format.

Flow continues to S304 if the determination at S303 is negative. The treatment beam parameters are changed at S304. The parameters may be changed automatically by treatment planning system S304 and/or by an operator. The parameters may be changed in order to reduce and/or otherwise modify the difference between the planned dose and the dose to be delivered. Accordingly, the dose to be delivered is again determined at S302 based on the changed parameters. In some embodiments, flow returns to S301 from S304 to acquire a new three-dimensional cone beam image and to thereafter proceed as described above.

Flow continues from S303 to S305 once the determination at S303 is affirmative. At S305, treatment radiation is delivered based on the current treatment beam parameters. Such delivery may comprise executing a treatment plan in order to control linac 110 based on the treatment beam parameters and other parameters/instructions specified by the treatment plan.

According to some embodiments of process 300, a patient position may be verified prior to S302. Verification of the position may be based on the three-dimensional image acquired at S301 and/or on conventional techniques such as those described in the Background.

Figure 8:
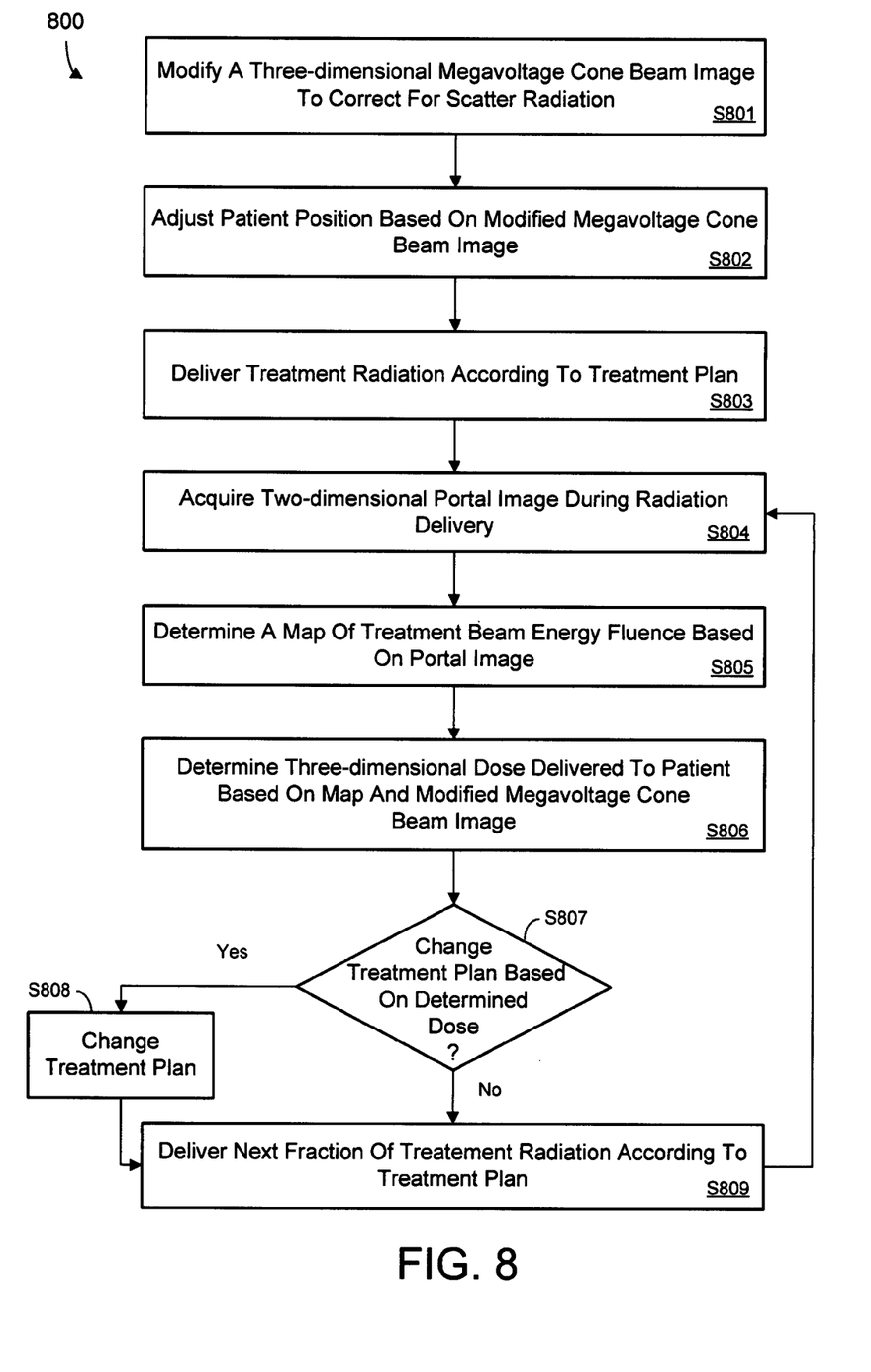
FIG. 8 comprises a flow diagram illustrating process steps according to some embodiments.

FIG. 8 is a flow diagram of process steps 800 according to some embodiments. Process steps 800 may be used to determine a delivered dose and to change a treatment plan based on the delivered dose.

A three-dimensional megavoltage cone beam image is modified at S801 to correct for scatter radiation. Some embodiments of S801 include acquisition of the three-dimensional cone beam image as described with respect to S301 of process 300.

Scatter radiation comprises deflected radiation that does not travel along an expected radiation trajectory from a radiation source to an imaging system. Therefore, scatter radiation received at a particular location of the imaging system does not reflect attenuative properties of all the tissues located along an expected trajectory from the radiation source to the particular location. As a result, received scatter radiation induces noise and reduces the intensity gradients (i.e., contrast) between image areas that represent different objects in an image. Although any suitable technique may be used at S801, various embodiments to modify the three-dimensional cone beam image to correct for scatter radiation will be discussed in detail with respect to FIGS. 9 through 11.

A position of a patient is adjusted at S802 based on the modified three-dimensional cone beam image. For example, the image or a two-dimensional slice thereof, may be compared with a previously-acquired image that reflects desired patient positioning for delivery of radiation according to a treatment plan. The previously-acquired image may comprise a conventional CT image based on which the treatment plan was generated. S802 may also include any conventional techniques for verifying and adjusting patient position.

Treatment radiation is delivered according to a treatment plan at S803. In some embodiments, linac 110 executes one of treatment plans 208 to deliver radiation according to parameters specified in the treatment plan. During delivery of the radiation, a two-dimensional portal image is acquired at S804. Imaging device 116 may acquire the portal image as described above. Some embodiments of S804 include, in addition to the corrections mentioned above, modification of the acquired portal image to correct for artifacts caused by scatter radiation and/or beam hardening. For example, a portal image of a uniformly dense volume (e.g., a water phantom) may show greater intensities at its edges than at its center. Accordingly, such a portal image may be used to calibrate imaging device 116 to correct for any artifacts. Calibration may comprise determining a single pixel value associated with the image (e.g., an average value), and determining a correction value to be applied to each pixel of the image that will result in each pixel having the single value.

A map of treatment beam energy fluence is determined at S805 based on the corrected portal image. The map may be determined by converting the intensity values of the portal image to correspond with the attenuation caused by the physical electron densities. The conversion may be performed as described with respect to S301.

Next, at S806, a three-dimensional dose delivered to the patient is determined based on the map and the modified megavoltage cone beam image. According to some embodiments of S806, the intensity values of the modified three-dimensional megavoltage cone beam image are converted to physical electron density values as described above. Next, the map of energy fluence is back-projected through the converted three-dimensional cone beam image to determine the energy fluence entering the patient. Such a back projection may correct for $1/r^2$ fall-off and utilize the projection matrices P described with respect to FIG. 5. Finally, a dose calculation engine as described above calculates the dose based on the converted three-dimensional cone beam image and the determined entering energy fluence.

It is then determined at S807 whether the treatment plan should be changed based on the determined dose. The determination at S807 may be performed automatically based on pre-configured rules and/or may require operator judgment. The determination may utilize two-dimensional or three-dimensional renderings of isodose curves representing the delivered dose and the planned dose. In case of patient motion or deformation, it may be necessary to align the planning images with the treatment cone beam images by means of warping registration. This alignment may be included within S807.

For example, if the determined dose indicates that a first patient volume has received a larger dose than called for by the treatment plan, it may be determined to change the treatment plan to reduce the dose delivered to the first volume in subsequent treatment fractions. The treatment plan may then be changed accordingly at S808.

A next fraction of megavoltage radiation is delivered at S809 according to the treatment plan, regardless of whether or not the plan was changed at S808. Flow then returns to S804 and continues as described above. Accordingly, the treatment plan may continue to be changed as successive fractions are delivered.

Figure 9:
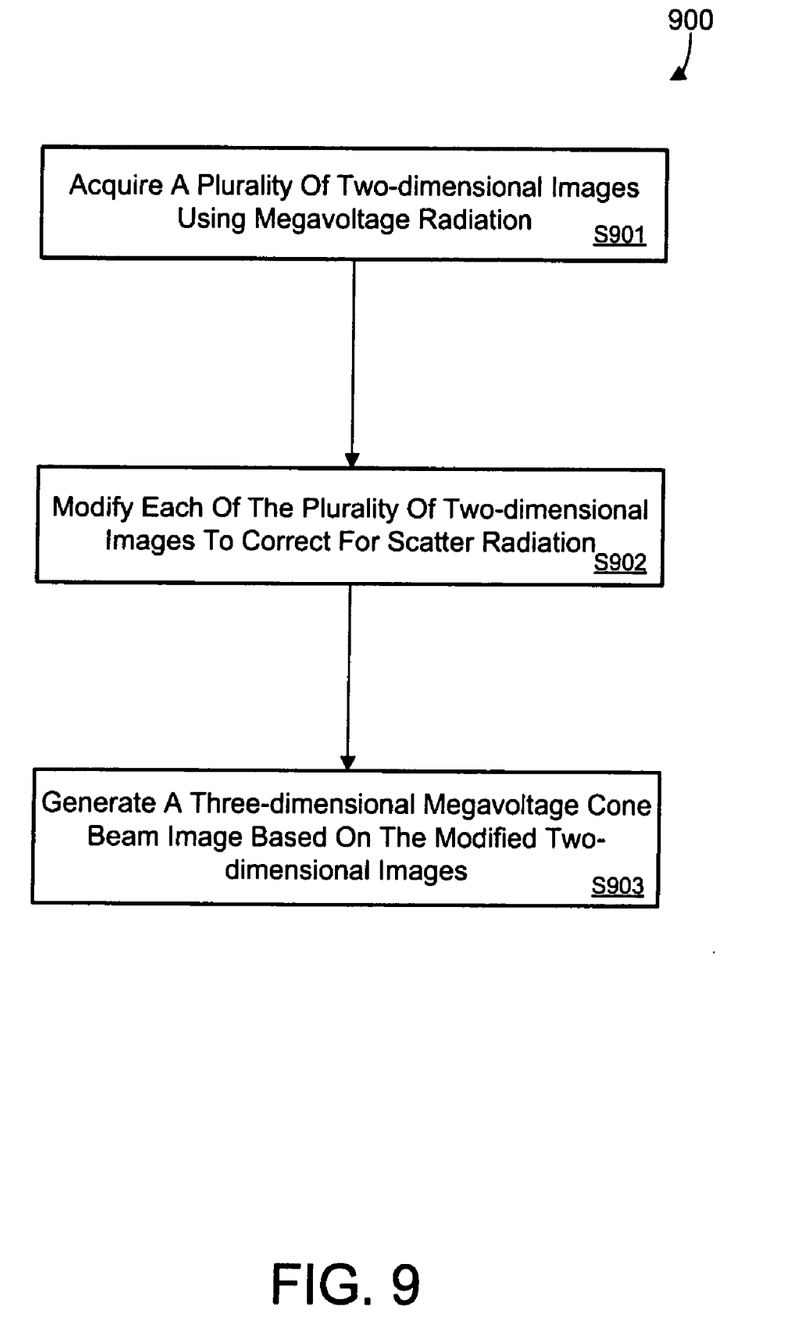
FIG. 9 comprises a flow diagram illustrating process steps according to some embodiments.

Process 900 of FIG. 9 comprises modification of a three-dimension megavoltage cone beam image to correct for scatter radiation according to some embodiments of S801. Initially, at S901, a plurality of two-dimensional images are acquired using megavoltage radiation. The two-dimensional images may comprise portal images acquired by imaging device 116 during rotation of gantry 112 as described above.

Each of the plurality of two-dimensional images is modified at S902 to correct for scatter radiation. Such correction may proceed as described above with respect to S804, but embodiments are not limited thereto. Next, a three-dimensional megavoltage cone beam image is generated at S903 based on the modified two-dimensional images. Generation of the three-dimensional image may proceed as described with respect to S301. For example, the image may be generated using standard CT techniques, and may account for projection matrices P illustrated in FIG. 5.

Figure 10:
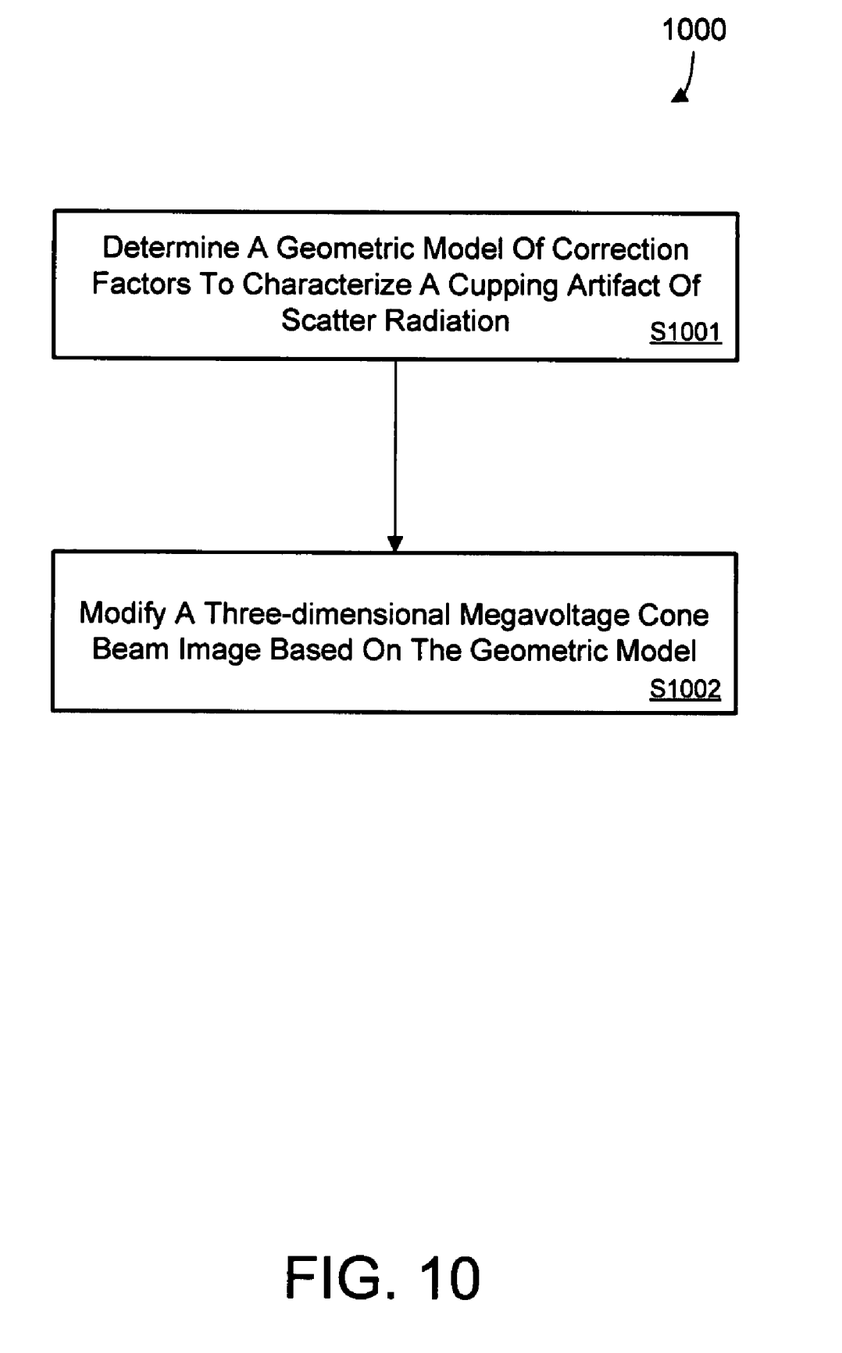
FIG. 10 comprises a flow diagram illustrating process steps according to some embodiments.

Process 1000 comprises modification of a three-dimensional megavoltage cone beam image to correct for scatter radiation according to further embodiments. A geometric model of correction factors is first determined at S1001. The geometric model characterizes a cupping artifact of scatter radiation.

For example, a three-dimensional megavoltage cone beam image of a head-sized water cylinder may be acquired at S1001 in order to characterize a cupping artifact of scatter radiation produced during acquisition of a three-dimensional megavoltage cone beam image of a head-and-neck. The average pixel value of image is determined, and a basic ellipsoid shape (semiaxes; $r_x, r_y, r_z$) centered on the cylinder ($x_c, y_c, z_c$) is defined to satisfy the equation: $(x-x_c/r_x)^2+(y-y_c/r_y)^2+(z-z_c/r_z)^2=\alpha^2 \rightarrow CF_\alpha$. Correction factors are determined for any desired number (e.g., eight) values of $\alpha$. Linear interpolation or extrapolation may be used to determine correction factors for values of $\alpha$ that lie between or beyond the determined values. The three-dimensional megavoltage cone beam image is then modified at S1002 based on the geometric model.

Figure 11:
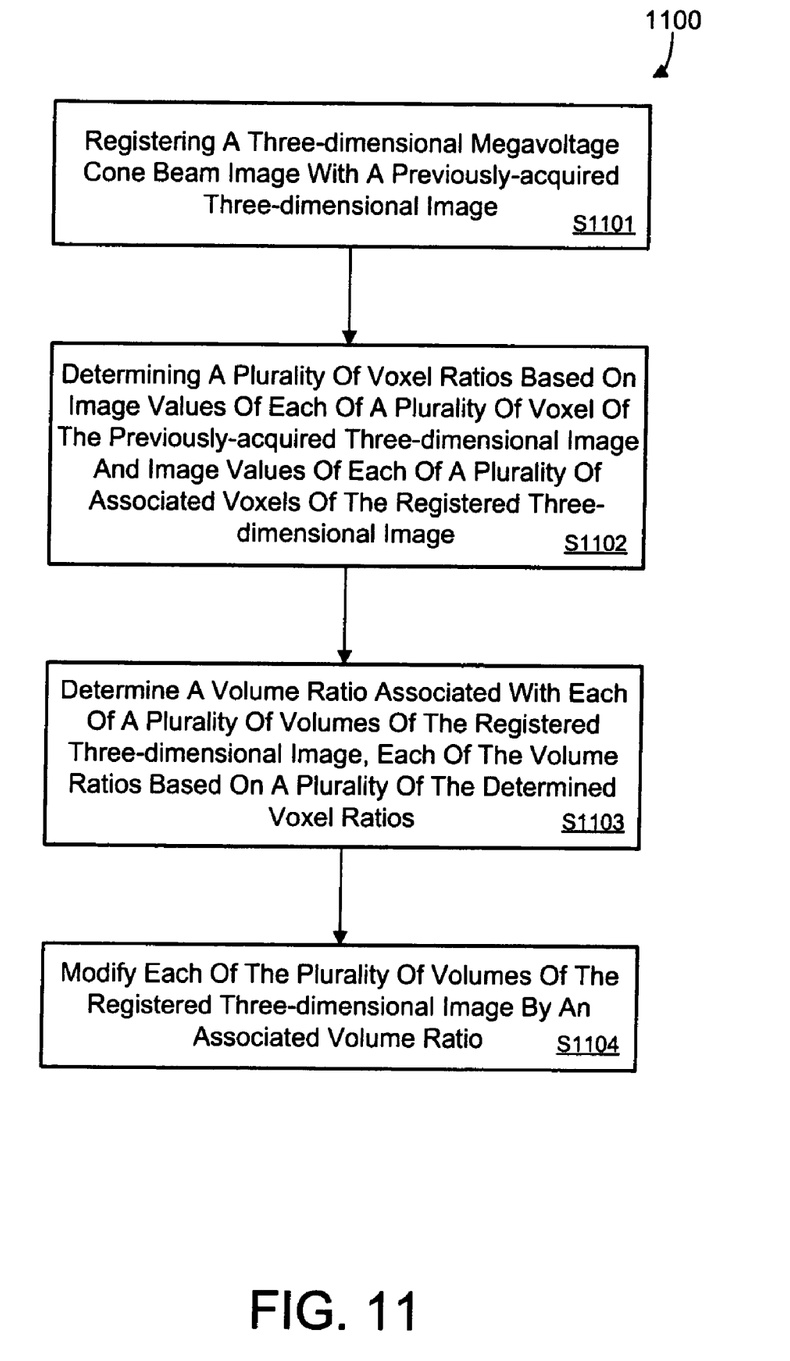
FIG. 11 comprises a flow diagram illustrating process steps according to some embodiments.

Process 1100 of FIG. 11 comprises yet another process to modify a three-dimensional megavoltage cone beam image to correct for scatter radiation according to some embodiments.

In particular, a three-dimensional megavoltage cone beam image is registered with a previously-acquired three-dimensional image at S1101. The registration may proceed according to any image registration process that is or becomes known, and the previously-acquired image may comprise an image acquired by a conventional CT scanner. A plurality of voxel ratios are then determined at S1102. Specifically, for each voxel location, a ratio is determined between the value of a voxel of the previously-acquired three-dimensional image that exists at the voxel location and the value of a voxel of the registered three-dimensional image that exists at the voxel location.

A volume ratio associated with each of a plurality of volumes of the registered three-dimensional image is determined at S1103 based on a plurality of the determined voxel ratios. For example, a volume of the registered three-dimensional image is composed of several voxels, each of which is associated with a voxel ratio determined at S1102. The voxel ratios of the volume may be eroded, dilatated and/or averaged to generate a single volume ratio associated with the volume.

Next, each of the plurality of volumes of the registered three-dimensional image is modified by an associated volume ratio at S1104. According to some embodiments, all voxels of a volume are multiplied by a volume ratio associated with the volume at S1104.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
   acquiring a three-dimensional cone beam image; and
   determining a dose to be delivered based on the three-dimensional image and on parameters of a treatment beam to deliver the dose,
   wherein determining the dose comprises:
   determining an electron density value associated with each of a plurality of voxels of a modified three-dimensional cone beam image;
   delivering treatment radiation according to a treatment plan;
   acquiring a portal image during delivery of the radiation;
   determining a map of treatment beam energy fluence based on the portal image;
   determining an entry dose based on the map of treatment beam energy fluence and the electron density value associated with each of the plurality of voxels; and
   determining the dose delivered to each of the plurality of voxels based on the entry dose and the electron density value associated with each of the plurality of voxels.

2. A method according to claim 1, further comprising:
   changing the parameters of the treatment beam to second parameters based on the determined dose.

3. A method according to claim 2, wherein changing the parameters of the treatment beam based on the determined dose comprises:
   spatially registering the determined dose with a planned dose;
   determining a difference between the spatially-registered determined dose and the planned dose; and
   determining the second parameters based on the determined difference.

4. A method according to claim 1, wherein acquiring the three-dimensional cone beam image comprises:
   acquiring a plurality of two-dimensional images using megavoltage radiation; and
   generating a three-dimensional image based on the plurality of two-dimensional images.

5. A method comprising:
   modifying a three-dimensional cone beam image to correct for scatter radiation; and
   determining a dose based on the modified three-dimensional cone beam image,
   wherein modifying the three-dimensional cone beam image comprises:
   registering the three-dimensional cone beam image with a previously-acquired three-dimensional image;
   determining a plurality of voxel ratios based on image values of each of a plurality of voxels of the previously-acquired three-dimensional image and image values of each of a plurality of associated voxels of the registered three-dimensional image; and
   determining a volume ratio associated with each of a plurality of volumes of the registered three-dimensional image, each of the volume ratios based on a plurality of the determined voxel ratios; and
   modifying each of the plurality of volumes of the registered three-dimensional image by an associated volume ratio.

6. A method according to claim 5, further comprising:
   changing a next treatment fraction based on the determined dose.

7. A method according to claim 6, wherein changing the next treatment fraction based on the determined dose comprises:
   determining a difference between the determined dose and a planned dose; and
   changing the next treatment fraction based on the difference.

8. A method according to claim 5, wherein modifying the three-dimensional cone beam image to correct for scatter radiation comprises:
   acquiring a plurality of two-dimensional images using megavoltage radiation;
   modifying each of the plurality of two-dimensional images to correct for scatter radiation; and
   generating the three-dimensional cone beam image based on the modified two-dimensional images.

9. A method according to claim 5, wherein modifying the three-dimensional cone beam image comprises:
   determining a geometric model of correction factors to characterize a cupping artifact of scatter radiation; and
   modifying the three-dimensional cone beam image based on the geometric model.

10. A method according to claim 5, wherein the previously-acquired three-dimensional image is acquired by a computed tomography scanner.

11. An apparatus comprising:
    a linear accelerator to generate a treatment radiation beam associated with a plurality of treatment beam parameters;
    a portal imaging device to acquire a plurality of two-dimensional images based on the treatment radiation beam; and
    a processor to generate a three-dimensional image based on the plurality of two-dimensional images, and to determine a dose to be delivered by the treatment radiation beam based on the three-dimensional image and on the plurality of treatment beam parameters,
    wherein determination of the dose comprises:
    determination of an electron density value associated with each of a plurality of voxels of a modified three-dimensional cone beam image;
    delivery of treatment radiation according to a treatment plan;
    acquisition of a portal image during delivery of the radiation;
    determination of a map of treatment beam energy fluence based on the portal image;
    determination of an entry dose based on the map of treatment beam energy fluence and the electron density value associated with each of the plurality of voxels; and
    determination of the dose delivered to each of the plurality of voxels based on the entry dose and the electron density value associated with each of the plurality of voxels.

12. An apparatus according to claim 11, wherein the processor is to change at least one of the plurality of treatment beam parameters based on the determined dose.

13. An apparatus according to claim 12, wherein the processor is to change at least one of the plurality of treatment beam parameters by:
    spatially registering the determined dose with a planned dose;

determining a difference between the spatially-registered determined dose and the planned dose; and determining at least one new treatment beam parameter based on the determined difference.

14. An apparatus comprising:

a linear accelerator to generate a treatment radiation beam;

a portal imaging device to acquire a plurality of two-dimensional images based on the treatment radiation beam; and a processor to modify a three-dimensional cone beam image to correct for scatter radiation and to determine a dose based on the modified three-dimensional cone beam image, wherein modification of the three-dimensional cone beam image comprises:

registration of the three-dimensional cone beam image with a previously-acquired three-dimensional image;

determination of a plurality of voxel ratios based on image values of each of a plurality of voxels of the previously-acquired three-dimensional image and image values of each of a plurality of associated voxels of the registered three-dimensional image; and determination of a volume ratio associated with each of a plurality of volumes of the registered three-dimensional image, each of the volume ratios based on a plurality of the determined voxel ratios; and modification of each of the plurality of volumes of the registered three-dimensional image by an associated volume ratio.

15. An apparatus according to claim 14, the processor further to change a next treatment fraction based on the determined dose.

16. An apparatus according to claim 15, wherein changing the next treatment fraction based on the determined dose comprises:

determining a difference between the determined dose and a planned dose; and changing the next treatment fraction based on the difference.

17. An apparatus according to claim 14, wherein modifying the three-dimensional cone beam image to correct for scatter radiation comprises:

acquiring a plurality of two-dimensional images using megavoltage radiation;

modifying each of the plurality of two-dimensional images to correct for scatter radiation; and generating the three-dimensional cone beam image based on the modified two-dimensional images.

18. An apparatus according to claim 14, wherein modifying the three-dimensional cone beam image comprises:

determining a geometric model of correction factors to characterize a cupping artifact of scatter radiation; and modifying the three-dimensional cone beam image based on the geometric model.

19. An apparatus according to claim 14, wherein the previously-acquired three-dimensional image is acquired by a computed tomography scanner.

* * * * *